(12) United States Patent
Choi et al.

(10) Patent No.: US 8,569,008 B2
(45) Date of Patent: Oct. 29, 2013

(54) MULTIFUNCTIONAL BIOMEMORY DEVICE

(75) Inventors: Jeong Woo Choi, Seoul (KR); Taek Lee, Seoul (KR); Jun Hong Min, Seongnam-si (KR)

(73) Assignee: Industry-University Cooperation Foundation Sogang University, Seoul (KR)

( * ) Notice: Subject to any disclaimer, the term of this patent is extended or adjusted under 35 U.S.C. 154(b) by 0 days.

(21) Appl. No.: 13/404,696

(22) Filed: Feb. 24, 2012

(65) Prior Publication Data

US 2013/0029396 A1    Jan. 31, 2013

(30) Foreign Application Priority Data

Jul. 29, 2011    (KR) .......................... 10-2011-0075570

(51) Int. Cl.
*C12Q 1/26* (2006.01)
(52) U.S. Cl.
USPC ............................................ 435/25; 435/189
(58) Field of Classification Search
USPC ................................................... 435/25, 189
See application file for complete search history.

(56) References Cited

U.S. PATENT DOCUMENTS

2006/0194343 A1* 8/2006 Martin et al. .................. 436/518
2010/0270543 A1* 10/2010 Choi et al. ....................... 257/40

FOREIGN PATENT DOCUMENTS

| KR | 10-2009-0068075 | 6/2009 |
|---|---|---|
| WO | WO-2009082064 A1 | 7/2009 |

OTHER PUBLICATIONS

Kim, Sang-Uk et al. Nanoscale Film Formation of Recombinant Azurin Variants with Various Cysteine Residues . . . J Nanoscience Nanotechnology 10(5)3241-5, May 2010.*
Kim Sang-Uk et al. Nanoscale Film Formation of Ferritin and Its Application to Biomemory Device. Ultramicroscopy 109(8)974-979 2009.*
Yagati A. et al. Multi-Bit Biomemory Consisting of Recombinant Protein Variants, Azurin. Biosensors Bioelectronics 24(5)1503-1507, 2009.*
Choi J. et al. Protein Based Biomemory Device Consisting of the Cysteine Modified Azurin. Applied Physics Letters 91(26)263902/1-/3, 2007.*
Choi et al. "Bioelectronic Device Consisting of Cytochrome c/poly-L-aspartic Acid Adsorbed hetero-Langmuir-Blodgett Films," J. Biotechnol. 94:225-233, 2002.
Kim et al., "Nanoscale Protein-Based Memory Device Composed of Recombinant Azurin," Biomaterials 31:1293-1298, 2010.
Lee et al., "Multilevel Biomemory Device Consisting of Recombinant Azurin/Cytochrome C," Adv. Mater. 21:1-5, 2009.
Notice of Grounds for Rejection for Korean Patent Application 10-2011-0075570, dated Nov. 9, 2012, English Language translation provided (6 pages).

* cited by examiner

*Primary Examiner* — Ralph Gitomer
(74) *Attorney, Agent, or Firm* — Clark & Elbing LLP

(57) ABSTRACT

The present disclosure relates to a multifunctional biomemory device in which a protein having a redox potential substituted with a metal ion is directly immobilized on a substrate. The present disclosure provides an operating method in which the redox state of the protein is controlled by applying three different potentials. The present disclosure provides a biomemory device in which the metal ion of a metalloprotein is substituted to allow for artificial control of the redox potential. The present disclosure provides a new-concept biomemory device as an information storage device based on the principle of electron transfer of a naturally occurring biomolecule.

1 Claim, 8 Drawing Sheets

MULTIFUNCTIONAL BIOMEMORY DEVICE

This application claims benefit of priority to Korean application 10-2011-0075570 filed Jul. 29, 2011.

TECHNICAL FIELD

The present disclosure relates to a multifunctional biomemory device in which a protein having a redox potential substituted with a metal ion is directly immobilized on a substrate.

BACKGROUND ART

In the field of biotechnology, nanotechnology and electrical engineering are being utilized to develop new-type electronic devices such as chips, sensors and actuators.[1-4] As a result of this work, a new scientific area called molecular electronics has emerged. Molecular electronics involves the combination of biotechnology and nanotechnology for expansion into information technology.

Traditionally, protein molecules have been shown to perform important roles in various biological systems. However, protein molecules can now also be used as an important element in human-designed electronic devices such as biosensors, transistors or memory devices. In addition, several hypotheses have been proposed for the design of electronic devices that are based on organic molecules and biomolecules.[5-10] However, the devices developed in these studies only displayed a simple function and could not perform multiple functions.

Previously, the inventors of the present disclosure developed a simple electronic device that consisted of biomolecular hetero Langmuir-Blodgett films. This device displayed switching functions and could be used as a molecular diode.[11,12] After the development of this initial device, the inventors of the present disclosure studied electroactive systems in regard to the kinetics of electron transport for further applications such as biosensors and bioelectronic devices. More recently, the inventors of the present disclosure focused on the development of various electrochemical-based biomemory devices that consist of cysteine-modified azurin and cytochrome c.[17,18] However, the proposed biomemory device only displayed one function and only one bit information could be controlled. Therefore, the inventors of the present disclosure attempted to overcome the limitation of current bioelectronic devices, which do not have the ability to perform multiple functions. The biomemory chip of the present disclosure can perform multiple functions since it can exist in 2-state and 3-state (WRER-type and WORM-type).

In the present disclosure, a cysteine-modified azurin was designed using the site-directed mutagenesis technique and 4 different metal ions were introduced to make a 4-bit biomemory chip capable of performing multiple functions. The recombinant protein containing a cysteine residue and different metal substituents was designed and directly immobilized on gold surface without any chemical linkers. The redox property of the 4 different azurin variants (Co-substituted type, Ni-substituted type, Fe-substituted type and Mn-substituted type) was measured. The presence of the different metal substituents in the recombinant azurin protein was confirmed by UV-VIS spectroscopy. In addition, the surface morphology of the device was investigated by atomic force microscopy (AFM). The electrochemical properties of the 4 different azurin variants were assessed by cyclic voltammetry (CV) and open-circuit potential. In this analysis, the recombinant azurin variants were shown to be successfully modified by metal ion substitution. The natural property of each material and coordinated metal and electron transfer kinetics between the material and the substrate were the reason of the change in redox properties. As memory elements, the substituted metal ions could be used to store different information because they have different conducting states. In addition, the inflow and outflow of electrons could be easily controlled by applying an external potential. The memory functions of this device were verified by chronoamperometry (CA) and open-circuit potential amperometry (OCPA). In their previous study, the inventors of the present disclosure proposed the basic concept of this biomemory device.[17] In the present disclosure, they confirmed the electrochemical properties of each modified azurin variant and developed a multifunctional 4-bit bio memory device using the recombinant azurin variants. If the characteristics of the different azurin variants were applied and integrated, a multifunctional biomolecule memory device would be realized. The control of immobilization of each azurin variant on the micro scale will be a vital factor. A computerized multi-channel electrochemical workstation is one possible application of the device of the present disclosure. It acquires various electrochemical data from each channel at the time and displays the results in parallel. This will be compared with a parallel result from each device and then integrated for operation as an independent working memory cell. FIG. 1 shows a schematic diagram of the 4-bit biomemory chip containing the recombinant azurin variants and its mechanism.

Throughout the specification, a number of publications and patent documents are referred to and cited. The disclosure of the cited publications and patent documents is incorporated herein by reference in its entirety to more clearly describe the state of the related art and the present disclosure.

DISCLOSURE

Technical Problem

The inventors of the present disclosure have made efforts to develop a biomemory device in which a protein having a redox potential substituted with a metal ion is immobilized on a substrate, especially a device capable of exhibiting memory device functions such as "read", "write" and "erase". As a result, they have developed a multifunctional biomemory device exhibiting "read", "write" and "erase" functions by substituting a recombinant protein having a cysteine residue with a metal ion.

The present disclosure is directed to providing a biomemory device in which a protein having a redox potential substituted with a metal ion is immobilized on a substrate.

The present disclosure is also directed to providing a biomemory device exhibiting different memory functions.

The present disclosure is also directed to providing a biomemory device having a bit number of 4 or more.

Other features and aspects will be apparent from the following detailed description, drawings and claims.

Technical Solution

In one general aspect, the present disclosure provides a biomemory device in which a protein having a redox potential substituted with a metal ion is directly immobilized on a substrate.

The inventors of the present disclosure have studied to realize an electronic device using biomolecules, especially one capable of exhibiting memory device functions such as "read", "write" and "erase". They have confirmed that a biomemory device exhibiting "read", "write" and "erase" functions can be provided by introducing a metal ion to a recombinant protein having a cysteine residue which has a redox potential and can be directly immobilized to a substrate to form a self-assembled monolayer (SAM).

One of the most prominent features of the present disclosure is that a protein having a redox potential is directly immobilized on the surface of a substrate to use as an electronic device.

In an exemplary embodiment of the present disclosure, the protein is a recombinant protein having a redox potential and has a cysteine residue introduced at the N- or C-terminal of the recombinant protein. The recombinant protein is directly immobilized on the substrate by means of the thiol group of the cysteine residue.

Another feature of the present disclosure is that a protein biomolecule having a redox potential is used as a memory device and a cysteine residue is introduced at the N- or C-terminal of the protein to form a stable self-assembled monolayer (SAM) on a substrate. The introduced cysteine residue forms a stable monolayer with good orientation by means of its thiol group on a substrate, specifically on a metal substrate, more specifically on a gold (Au) substrate.

In an exemplary embodiment of the present disclosure, the recombinant protein has 2-10 cysteine residues. If the number of the introduced cysteine residues is less than 2, i.e. one, the function of the cysteine residue as an anchoring site decreases greatly. And, if the number of the cysteine residues exceeds 10, disulfide bonds formed between the introduced cysteine residues make purification of the recombinant protein difficult and greatly decrease the function of the cysteine residues as an anchoring site.

In another exemplary embodiment of the present disclosure, the recombinant protein has 2-3 cysteine residues, most specifically 2 cysteine residues.

The protein is directly immobilized via the thiol group of the introduced cysteine. As used herein, the term "direct immobilization" refers to immobilization of a protein molecule directly on a substrate without help from another linker.

The direct immobilization is advantageous in that unnecessary resistance layers can be decreased in electron transfer process and immobilization capacity can be maximized under given conditions.

A linker is most commonly used at present as a technique to immobilize a protein on a substrate. However, this method has disadvantages of (i) requiring much excessive processes, (ii) exhibiting low immobilization rate and (iii) generating the insulating effect of linker layers.

The direct immobilization may overcome the defects of the existing techniques.

The recombinant protein used as the memory device in the present disclosure may be any protein having a redox potential and capable of accepting or releasing an electron. For example, the recombinant protein suitable to the present disclosure includes, but is not limited to, a metalloprotein containing a metal ion, such as flavodoxin, plastocyanin, thioredoxin, etc.

In an exemplary embodiment of the present disclosure, the recombinant protein having a redox potential is a metalloprotein containing a metal ion, more specifically azurin, hemoglobin, myoglobin, hemerythrin, cytochrome, iron-sulfur protein, rubredoxin, plastocyanin, ferritin, ceruloplasmin, carbonic anhydrase, vitamin $B_{12}$-dependent enzyme, nitrogenase, superoxide dismutase, chlorophyll-containing protein, calmodulin, glucose 6-phosphatase, hexokinase, DNA polymerase, vanabin, arginase, catalase, hydrogenase, iron-responsive element-binding protein, aconitase, urease, cytochrome oxidase, laccase, alcohol dehydrogenase, carboxypeptidase, aminopeptidase, β-amyloid, nitrate reductase, glutathione peroxidase, metallothionein or phosphatase, more specifically azurin, cytochrome a, cytochrome b or cytochrome c, most specifically azurin.

The metal ion of the metalloprotein may be substituted with magnesium, vanadium, manganese, iron, nickel, copper, zinc, molybdenum, cobalt, gallium, bismuth, gold, aluminum, platinum, chromium, silver, antimony, thallium, cadmium, mercury, lead, calcium or selenium, more specifically with cobalt, manganese, iron or nickel.

The recombinant azurins used in the present disclosure is are Co-type azurin, Ni-type azurin, Fe-type azurin and Mn-type azurin.

The substrate used in the biomemory device of the present disclosure may be any one used in the fabrication of memory devices. In an exemplary embodiment of the present disclosure, the substrate is a metal, metal oxide, glass, ceramic, quartz, silicon, semiconductor, $Si/SiO_2$ wafer, germanium, gallium arsenide, carbon, carbon nanotube, polymer, sepharose or agarose substrate, more specifically a metal substrate, most specifically a gold (Au) substrate.

As used herein, the term "gold substrate" refers to a substrate having a surface coated with gold.

A method for immobilizing the cysteine-modified protein on the substrate is described in detail as follows.

First, a substrate, specifically a gold substrate, is annealed at high temperature and cleaned with piranha solution. Then, the metal-substituted protein is dispersed on the gold substrate and allowed to stand so that a SAM is formed on the substrate. As a result, a protein-immobilized substrate is obtained.

In the layer of the recombinant azurin variant prepared according to the present disclosure, the Co-type azurin, Ni-type azurin, Fe-type azurin or Mn-type azurin forms small clusters with an average size of 20-40 nm.

In an exemplary embodiment of the present disclosure, the biomemory device of the present disclosure is operated by applying a reduction potential, an open-circuit potential and an oxidation potential.

In an exemplary embodiment of the present disclosure, the device of the present disclosure further comprises an electric field source.

One of the features of the present disclosure is that the cysteine-modified protein molecules are self-assembled on the substrate, specifically the gold substrate, through the thiol group of the cysteine residue and are utilized as a nano-scale information storage device using the intrinsic electron transfer properties of the protein dependent on the applied voltage.

For the protein-based biomemory device of the present disclosure to be operated electrically, the memory device of the present disclosure may be a reversibly changeable and electrically readable electronic device comprising the followings. The electronic device comprises a substrate. The substrate is the same as described above and its surface is electrically coated with gold as described in the following examples. A redox active layer is formed on the substrate. The SAM of the cysteine-modified recombinant protein having a redox potential is used as the redox active layer in the present disclosure. The redox active layer is placed under specific electronic conditions, e.g. oxidation state or reduction state, by the recombinant protein. An electrode is connected to the redox active layer. The device of the present disclosure comprises an electric field source, e.g. a voltage supply unit, linked to the substrate, the electrode, or both. Flow of electrons is induced by a voltage or an electric beam supplied to the electric field source, thus enabling the memory function.

Thus, when the memory device of the present disclosure is constructed electrochemically, the device of the present disclosure comprises: (i) the substrate, (ii) the SAM as the redox active layer which is immobilized on the substrate and contains the cysteine residues introduced to the recombinant protein having a redox potential, (iii) the electrode linked to the redox active layer and (iv) the electric field source supplying the voltage or electric beam to the substrate and/or the electrode.

Hereunder is given a specific example wherein the biomemory device of the present disclosure is constructed electrochemically.

The present disclosure relates to an information storage device enabling to change the oxidation and reduction state of proteins immobilized by adjusting applied voltage according to an electrochemical method. The substrate having the protein layer is incubated in an electrolyte solution, e.g. a HEPES electrolyte. The substrate is operated by connecting to a potentiostat as a working electrode, and a reference electrode (e.g., Ag/AgCl) and a counter electrode (e.g., Pt) are incorporated into the electrolyte. The reference electrode is a reference to read the potential changes of the working electrode in the potentiostat during voltage sweep. The counter electrode is a passage of electrons flowing as a result of the control of potential by the potentiostat. Such a three-electrode system is one of the most commonly used systems in the field of electrochemistry. In the simple electrochemical system described above, a voltage-current curve is obtained using the cyclic voltammetry method. An open-circuit potential is measured to investigate the equilibrium potential of the electrochemical system constructed. The open-circuit potential refers to a potential difference formed due to the intrinsic property of the protein layer and the electrolyte in a voltage-free state, i.e. in a circuit-broken state, naturally reaching equilibrium in the constructed system. Based on the above principle, a system can be artificially made close to the equilibrium state by applying an open-circuit potential to the system if the open-circuit potential is known. To describe in more detail, after the protein is reduced by accepting electrons from the electrolyte as the reduction potential is applied to the protein layer, electrons are released while the protein returns to the equilibrium state as the open-circuit potential is applied. Conversely, after the protein is oxidized by releasing the electrons, it returns to the original potential state by accepting electrons when the open-circuit potential is applied. Therefore, the open-circuit potential allows to read the redox state of the protein layer.

The reduction potential of the metal-substituted azurin variants prepared by the present disclosure is 74.10±20.75 mV, 51.60±7.58 mV, 105.12±15.24 mV and 24.97±11.26 mV, respectively for the Co-type azurin, Ni-type azurin, Fe-type azurin and Mn-type azurin. The oxidation potential of the Co-type azurin, Ni-type azurin, Fe-type azurin and Mn-type azurin is 210.03±15.58 mV, 172.90±16.36 mV, 236.09±21.75 mV and 132.61±30.54 mV, respectively. And, the open-circuit potential of the Co-type azurin, Ni-type azurin, Fe-type azurin and Mn-type azurin is 182.11±23.16 mV, 121.42±19.98 mV, 154.76±31.44 mV and 104.26±27.67 mV, respectively.

In an exemplary embodiment of the present disclosure, the device of the present disclosure is a write once read many (WORM) type device or a write read erase read (WRER) type device.

As used herein, the term 'WORM' means a data storage technique where information, once written, cannot be modified. The WORM type device is used to prevent undesired erasing of the stored data. The WORM type device can be 'read' unlimitedly after the information is written. And, the term 'WRER' refers to a data storage technique where information can be written and read freely.

In an exemplary embodiment of the present disclosure, the 'read', 'write' and 'erase' functions are performed by controlling the three voltage states, i.e. the oxidation potential, the open-circuit potential and the reduction potential, of each azurin variant (FIG. 10).

In another general aspect, the present disclosure provides a method for fabricating a biomemory device exhibiting different memory functions, comprising: (a) substituting a metal ion of a protein having a redox potential with another metal ion; and (b) immobilizing the protein on a substrate.

In another general aspect, the present disclosure provides a method for fabricating a biomemory device having a bit number of 4 or more, comprising: (a) preparing 4 or more protein variants by substituting a metal ion of a protein having a redox potential with 4 or more other metal ions; and (b) immobilizing the 4 or more protein variants on a substrate.

As used herein, the term 'bit' means the basic, minimum unit of information for storage. As used herein, the term 'bit number of 4 or more' means a storage capacity capable of storing 16 or more values.

In an exemplary embodiment, a 4-bit biomemory chip with 4 or more different metal ions introduced and thus capable of performing multiple functions is fabricated.

A detailed description about the method of the present disclosure will be omitted since it is similar to the description given above in regard to the biomemory device.

Advantageous Effects

The features and advantages of the present disclosure may be summarized as follows:

(a) The present disclosure provides a biomemory device in which a protein having a redox potential is directly immobilized on a substrate.

(b) The present disclosure provides an operating method in which the redox state of the protein is controlled by applying three different potentials.

(c) The present disclosure provides a biomemory device in which the metal ion of a metalloprotein is substituted to allow for artificial control of the redox potential.

(d) The present disclosure provides a new-concept biomemory device as an information storage device based on the principle of electron transfer of a naturally occurring biomolecule.

BEST MODE

Figure 1:
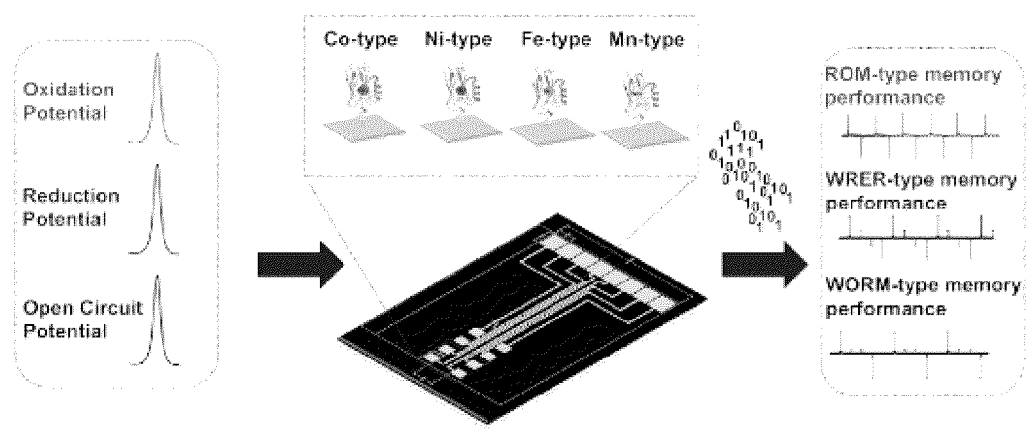
FIG. 1 schematically shows an operating mechanism of a biomemory chip of the present disclosure.

1. Materials and Methods 1.1 Genetic Engineering of *Pseudomonas aeruginosa* Azurin An *Escherichia coli* strain DH5a was used as the host for subcloning. Standard techniques were employed throughout this work. The gene encoding blue copper protein azurin was amplified using polymerase chain reaction (PCR) from the genomic DNA of *Pseudomonas aeruginosa*. The forward primer was designed to contain a NcoI restriction enzyme site and the reverse primer was designed to contain a BamHI restriction enzyme site The PCR product was purified using a DNA purification kit (QIAZEN, USA) and digested with two restriction enzymes for NcoI and BamHI (New England Biolabs, UK). The digested DNA fragments were ligated with a pET-21a(þ) vector (Novagen, Germany), which was predigested with NcoI and BamHI, using a ligation kit (TaKaRa, Japan). Azu Cys F and Azu Cys R primers were designed to contain a mutant site for site-directed mutagenesis (SDM) and used to change the codon for Lys92Cys (K92C) from AAG to TGC. Mutations in the azu gene were introduced using the SDM.[20]

1.2. Expression and Purification of Recombinant Azurin Variants

The plasmids, containing genes for azurins, were transformed into *E. coli* BL21 (DE3).[20] The transformants were grown to an OD of 0.6 at 37° C. in shake flasks containing 1 L of LuriaeBertani medium (0.5% yeast extract, 1.0% tryptophan, and 1.0% NaCl) with 50 mg/mL ampicillin. Expression was induced by adding isopropyl b-D-thiogalactopyranoside (IPTG) to a final concentration of 0.839 mM. The transformed cells were grown for an additional 16 h at 37° C. The cells were harvested by centrifugation at 5000 g for 15 min at 4° C. The cell paste was resuspended in sucrose buffer (20% sucrose, 0.3 M TriseHCl, pH 8.1, 1 mM EDTA) and subjected to osmotic shock (0.5 mM MgCl2). Contaminating proteins were precipitated from the periplasmic preparation by decreasing the pH to 3.8 (50 mM sodium acetate), yielding azurin-containing supernatant. Apo-azurin and cysteine-modified apo-azurin fractions (Elution pH ¼ 4.6 and 4.8, respectively) were separated on a CM excellulose ion-exchange column with a pH gradient from 4.0 to 6.0 (50 mM sodium acetate). To make azurin substitutes, the copper was removed by dialysis against 0.1 M KCN in 10 mM tris HCl, pH 7.0, for 7 days at room temperature. The azurin variants were prepared by adding metal ions [0.5 M CoCl2, 0.5 M NiCl2, 6H2O, 0.5 M FeCl2, nH2O, 0.5 M MnSO4] to the apoazurin solution. Metal uptake of apoazurin required 3 days at 4° C. The metal substitutes azurins were purified by MWCO 5 k Amicon Ultra centrifugal filter (Millipore, USA).[21,22]

1.3. Biomemory Chip Fabrication

To fabricate the biomemory chip as a working electrode, a gold working electrode was designed and fabricated on Si/SiO2 substrates using conventional fabrication methods on bulk scale. The electrode had an identical configuration, where the active area was square in shape with a side length of 1 mm and the electrical contact via Au pad had an area of 1.5 mm×2 mm. The starting material in this process was 4 inch silicon wafers (100) of the p-type (10e20 V cm$^{-1}$). The wafers were thermally oxidized to form an oxide coating 30 nm thick, then a layer of chrome (50 nm) and subsequently a layer of gold (200 nm) were evaporated on the silicon dioxide wafer surface, and, after etching the silicon nitride layer, the gold electrodes were formed. The fabricated Au electrode was cleaned in a piranha solution composed of 30 vol % H2O2 (Duksan Pure Chemical Co. Ltd., Korea) and 70 vol % H2SO4 (Daejung Chemical Co. Ltd., Korea) at 60 C for 5 min. The Au electrode was then rinsed with deionized water and dried under a stream of nitrogen.[20,21] Using these Au substrates, 20 ml of the azurin variants solution was dropped onto the Au substrate of the fabricated chip and incubated for 6 h to allow the recombinant azurins to form a covalent bond to the Au substrate. The water used for all experiments was distilled and deionized by Millipore. A 0.1 mg/ml recombinant azurin variants solution was prepared in 10 mMHEPES buffer at pH 7.0. HEPES solution was used as the electrolyte buffer.[19]

1.4. Investigating the Topography of Recombinant Azurin Variants Layer by AFM The surface morphology of the fabricated recombinant azurin variants was investigated by tapping-mode AFM (Digital instruments Nanoscope (R) IV, USA) at room temperature. These TM-AFM images were monitored using 1-10 Ω-cm Phosphorous (n) doped (Si) tips, which had a resonant frequency between 230 and 305 kHz. The image size was 500 nm×500 nm and a scan rate of 1.0 Hz was used to measure the surface morphology.

1.5. Electrochemical Experiments of Recombinant Azurin Variants Layer

This system was a conventional 3 electrodes system that consisted of a working electrode, counter electrode and reference electrode. The fabricated chip was used bought from BAS (USA) respectively. The electrochemical experiments were carried out with a CHI660A electrochemical workstation (CH Instruments, USA). All electrochemical experiments were carried out in the HEPES buffer solution.

2. Results and Discussion

2.1. Production of Recombinant Azurin Variants

Figure 2:
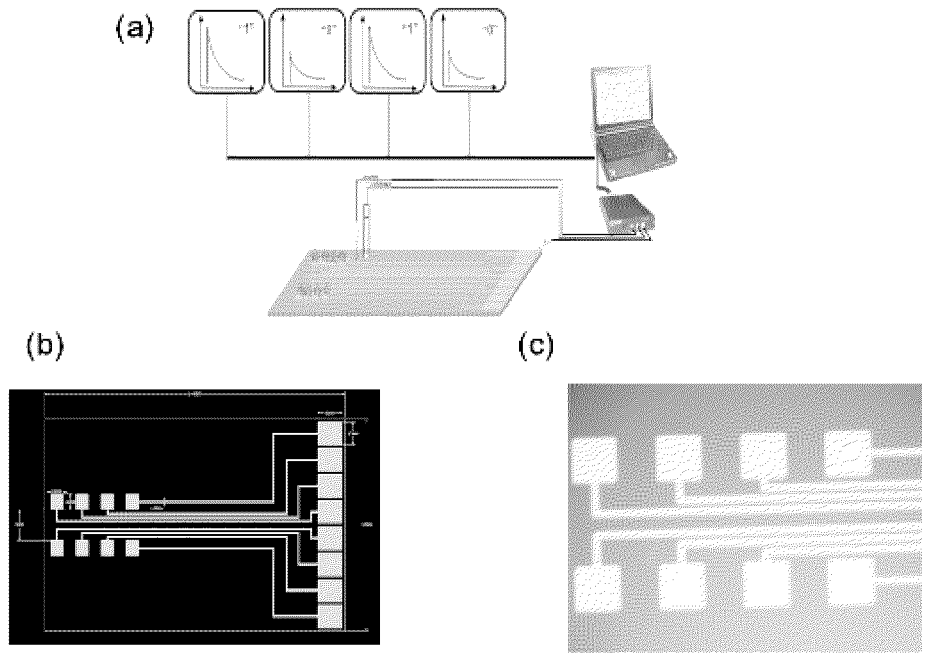
FIG. 2 systemically shows operating conditions. The memory device of the present disclosure is operated in a three-electrode system (a). (b) shows a CAD image of the biomemory chip, and (c) shows a photograph of the memory device. The biomemory device is used as a working electrode.
Figure 3:
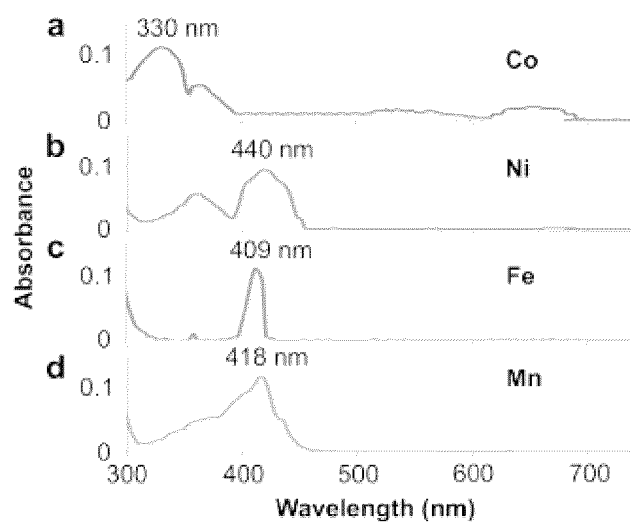
FIG. 3 shows UV-VIS absorption spectra of (a) Co-type azurin, (b) Ni-type azurin, (c) Fe-type azurin and (d) Mn-type azurin. Co-type azurin, Ni-type azurin, Fe-type azurin and Mn-type azurin show absorption peaks at 330 nm, 440 nm, 409 nm and 418 nm, respectively.

Expression of recombinant azurin variants and metal uptake (Co, Ni, Fe, Mn) by the folded cysteine-modified apoazurin was analyzed by UVeVIS spectroscopy. The *Pseudomonas aeruginosa* azurin is a small blue copper protein with a Greek-key topology. The recombinant azurin had a blue color due to the ligand-to-metal charge transfer between the cysteine sulfur ligand (Cys112) and the oxidized copper ion. The copper coordinates five residues (Gly45, His46, Cys112, His117, Met121) in a unique geometry that gives rise to an intense absorption at 627 nm.[21] In contrast, the absorbance of the Co-type azurin, Ni-type azurin Fe-type azurin and Mn-type azurin is at 330 nm, 440 nm, 409 nm and 418 nm, respectively. Thus, the UVeVIS spectra can be used to determine if the metals are bound. The results of metal-substituted azurin are shown in FIG. 2a,b,c,d, respectively.[22,23] Based on this analysis, the azurin variants shown to be well produced and could bind these metals (FIG. 3a-3d).

2.2. The Morphology Analysis of Recombinant Azurin Variants Layer by AFM

The surface morphologies of the recombinant azurin variants were investigated by AFM. FIG. 4a shows an AFM image of the cysteine-modified Co-type azurin layer when self-assembled on the Au surface. Small lumps 20-30 nm in size were observed on the surface. FIG. 4b depicts the AFM image of the recombinant Ni-type azurin layer. Similarly, 30-40 nm of Ni-type azurin clusters were well immobilized on the Au surface. Also, FIG. 4c and d show the topography of Fe-type and Mn-type azurin layers, respectively. Each azurin variant layer was well oriented and contained structures that were roughly between 20 nm and 40 nm. Thus, the different metals did not affect the assembly of the azurin variants. These results indicate that the cysteine-modified azurin variants were well arranged and organized on the Au surface without the need for an additional chemical linker.

2.3. The Speculation of Electrochemical Property

Figure 4:
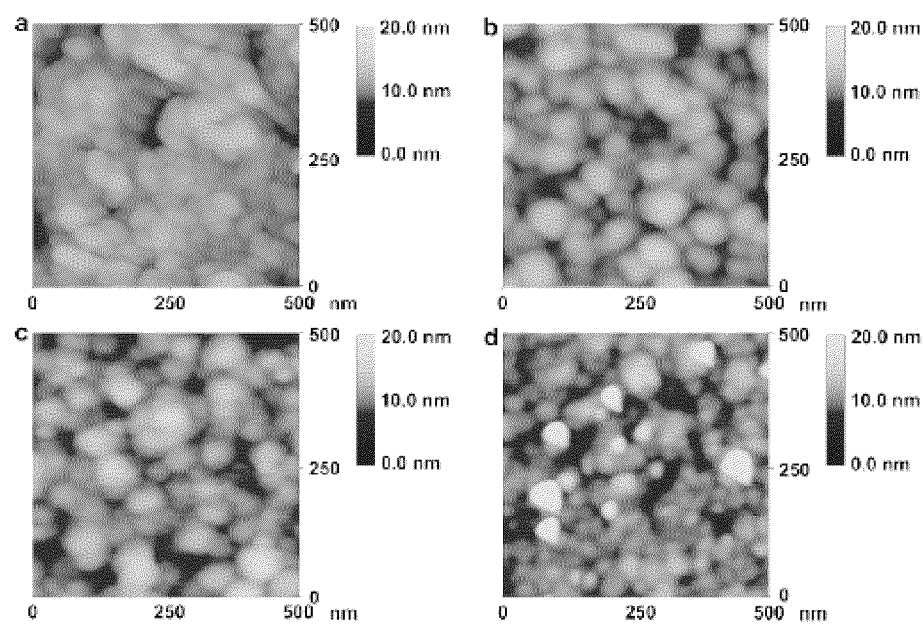
FIG. 4 shows surface topography of (a) Co-type azurin, (b) Ni-type azurin, (c) Fe-type azurin and (d) Mn-type azurin self-assembled on a gold substrate measured by atomic force microscopy.

We measured the redox properties of 4 different azurin variants (Ni type; Co type; Mn type; Fe-type). The purpose of these experiments was to examine the electrochemical properties of each modified azurin with the goal of assessing their potential to perform memory functions. In this regard, we assumed that the different metals would affect the electrochemical properties of the azurin variants. We initially measured the cyclic voltammetry (CV) of each self-assembled azurin variant layer. The results are shown in FIG. 4. We also measured the reduction potential and oxidation potential of all 10 modified azurin samples. Both peaks were clearly visible and coincident with normal azurin.[17] The reduction potential of the Co-type azurin, Ni-type azurin, Fe-type azurin and Mn-type azurin was 74.10±20.75 mV, 51.60 mV±7.85 mV, 105.12 mV±15.24 mV and 24.97 mV±11.26, respectively and the oxidation potential Co-type azurin, Ni-type azurin, Fe-type azurin and Mn-type azurin was 210.03±15.58 mV, 172.90 mV±16.36 mV, 236.09 mV±21.75 mV and 132.61 mV±30.54 mV, respectively. These results clearly indicate that the redox properties of azurin can be changed through metal substitution. The natural properties of each material, coordinated metal, electron transfer kinetics between material and substrate can change the redox properties of a compound. The structural and electrochemical redox properties have been previously shown to vary according to the coordinated metal ion, such as Ni(II), Cu(II), and Zn(II), which is located at the center of the porphyrin molecule. In this previous study the reduction and oxidation potential changed by about ±7.661% and ±8.757%, respectively.[24]

Figure 5:
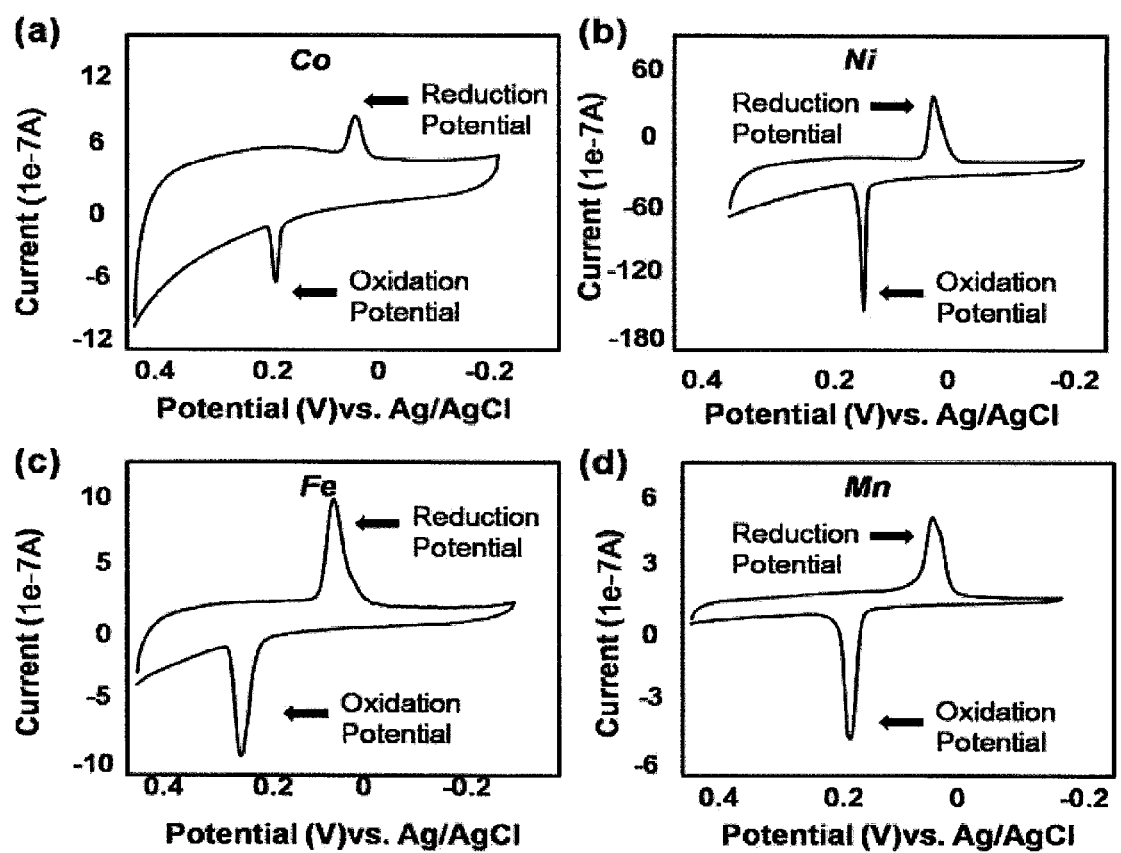
FIG. 5 shows a result of cyclic voltammetry of (a) Co-type azurin, (b) Ni-type azurin, (c) Fe-type azurin and (d) Mn-type azurin immobilized on a biomemory chip fabricated according to the present disclosure.

In addition, the OCP of each type of azurin was investigated. FIG. 5 depicts the open circuit potential (OCP) of each recombinant azurin. OCP is defined as the time required for the potential to equilibrate between electrolyte and azurin molecule. Generally, it decreases drastically from 1000 s as it approaches a specific potential based on Ag/AgCl. After 1000 s, the OCP approaches a specific potential where the potential is stabilized. The OCP of the Co-type azurin, Ni-type azurin, Fe-type azurin and Mn-type azurin was 182.11±23.16 mV, 121.42±19.98 mV, 154.76±31.44 mV, and 104.26±27.67 mV, respectively (FIG. 5a-5d). The time difference between these four different azurin variants was not significant because the 'OCP vs. time' data is entirely dependent on the initial conditions of the fabricated electrochemical cell. Sometimes the potential range needs to be significantly changed for stabilization, and other times only slight changes are needed. The final potential will vary in different cases depending on the initial conditions. Thus, only limited significance was applied to these results. This explanation will apply to all cases. Based on these results, we found that azurin variants self-assembled on prepared substrate displayed the appropriate electrochemical properties and retained their redox properties and OCP under different conducting states. As a result, further experiments will be conducted to assess memory performance.

2.4. The Assessment of 2-State Memory Function by CA

Figure 6:
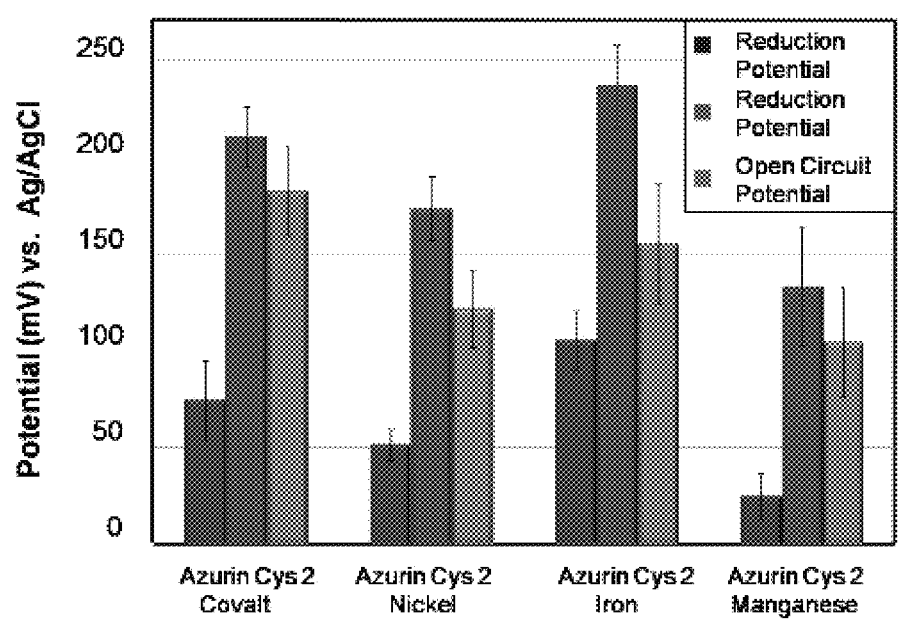
FIG. 6 shows a reduction potential, an oxidation potential and an open-circuit potential of each recombinant azurin variant (Co, Ni, Fe and Mn types). The blue bar represents the reduction potential and the red bar represents the oxidation potential. And, the green bar represents the open-circuit potential. The Co-type azurin has a reduction potential of 74.10±20.75 mV and an oxidation potential of 210.03±15.58 mV. The standard redox potential is 142.37 mV and the difference of the two potentials, i.e. the peak separation, is 136.53 mV. This value is related with potential sweeping as a simulation of the molecular switch. The Ni-type azurin has a reduction potential of 51.60±7.85 mV and an oxidation potential of 172.90±16.36 mV. The standard redox potential is 112.25 mV and the peak separation is 121.30 mV. The Fe-type azurin has a reduction potential of 105.21±15.24 mV and an oxidation potential of 236.09±21.75 mV. The standard redox potential is 170.61 mV and the peak separation is 130.97 mV. The Mn-type azurin has a reduction potential of 24.97±11.26 mV and an oxidation potential of 132.61±30.54 mV. The standard redox potential is 53.82 mV and the peak separation is 107.64 mV. Presumably, the redox potential of the azurin will vary depending on the substituted metal ion. This shows that each azurin has different conducting state.
Figure 7:
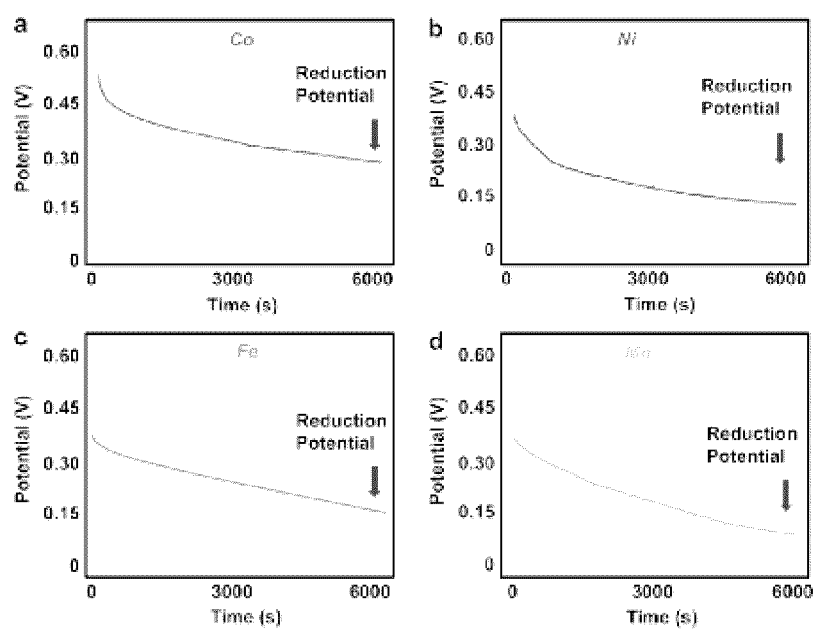
FIG. 7 shows the open-circuit potential of (a) Co-type azurin, (b) Ni-type azurin, (c) Fe-type azurin and (d) Mn-type azurin immobilized on a biomemory chip fabricated according to the present disclosure.
Figure 8:
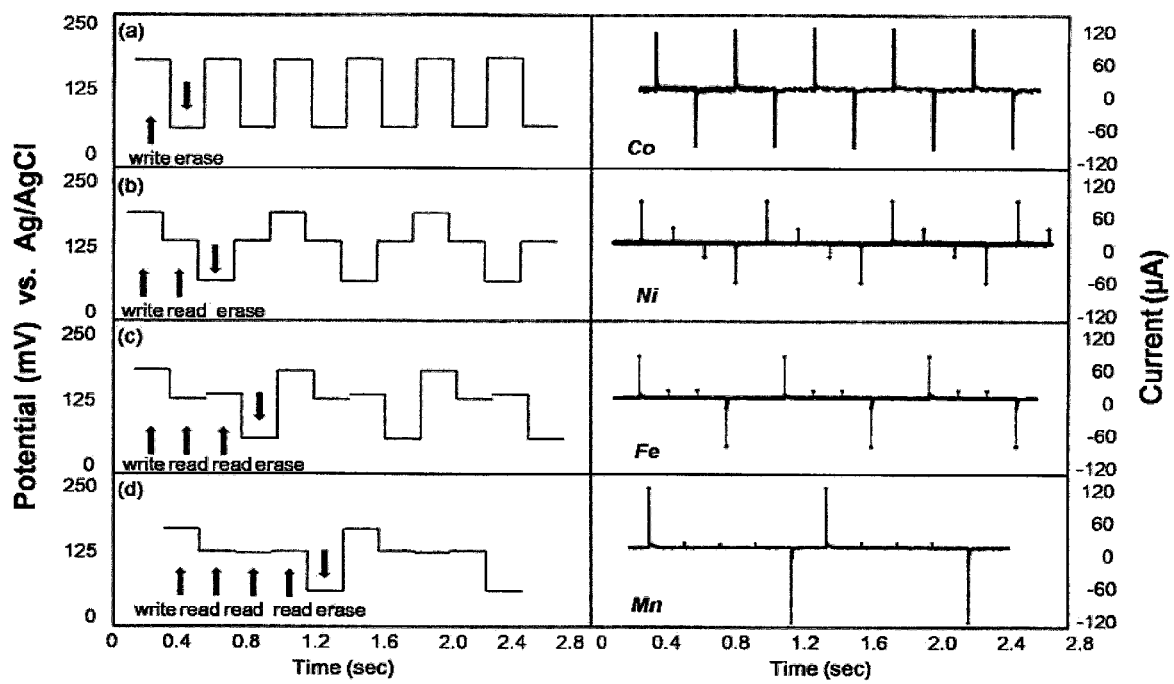
FIG. 8 shows a result of verifying the multifunctional memory performance of (a) Co-type azurin, (b) Ni-type azurin, (c) Fe-type azurin and (d) Mn-type azurin. The left part of the figure shows the applied oxidation potential, reduction potential and open-circuit potential, assigned to the 'write', 'read' and 'erase' functions, respectively. The right part of the figure displays the corresponding charging current observed for a total duration of 2.8 seconds.
Figure 9:
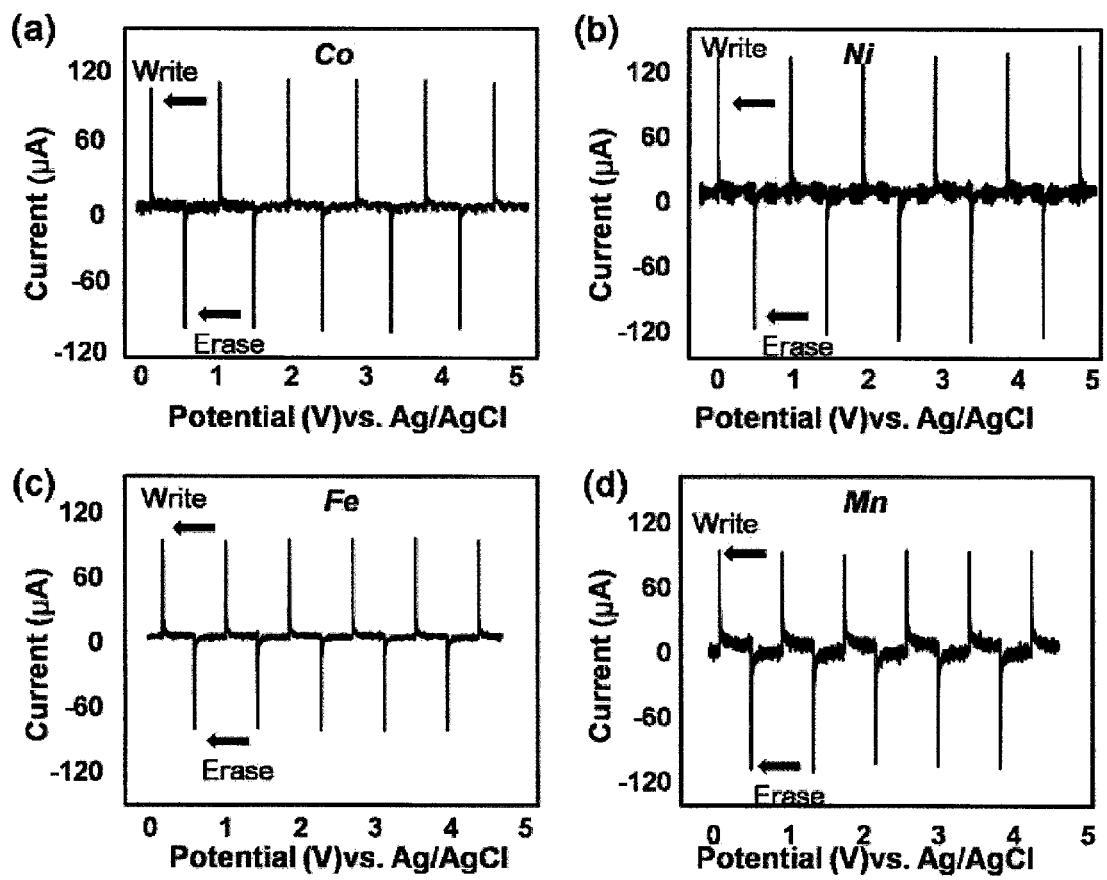
FIG. 9 shows a result of comparing current response of (a) Co-type azurin, (b) Ni-type azurin, (c) Fe-type azurin and (d) Mn-type azurin variants after applying the oxidation potential and reduction potential for test of 2-state biomemory function.
Figure 10:
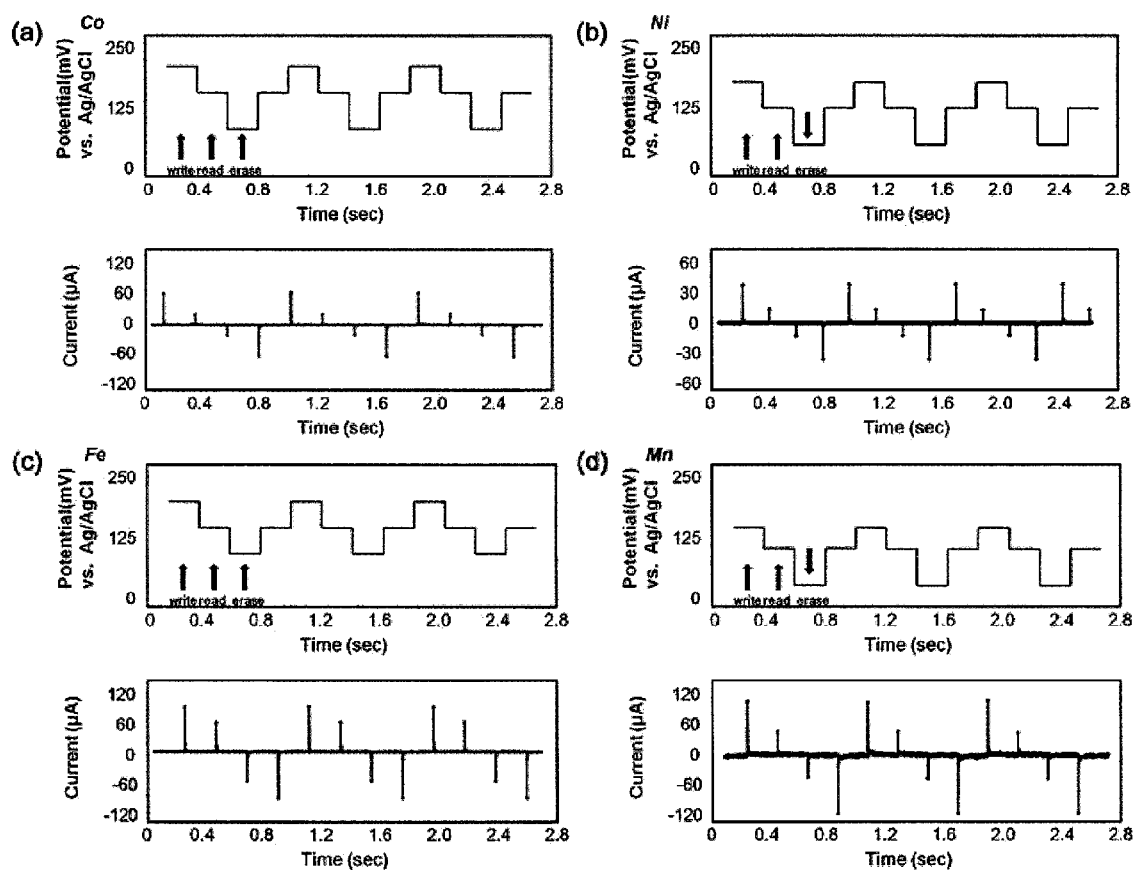
FIG. 10 shows a result of verifying the WRER-type memory function of (a) Co-type azurin, (b) Ni-type azurin, (c) Fe-type azurin and (d) Mn-type azurin by open-circuit potential voltammetry. The upper figures show the applied oxidation potential, oxidation potential, open-circuit potential and reduction potential, assigned to the 'write', 'read' and 'erase' functions, respectively. The lower figures show the corresponding charging current observed for a total duration of 2.8 seconds.

To assess the 2-state memory performance of this device, the chronoamperometry (CA) method was used. The CA method is an electrochemical technique in which the potential of the working electrode is stepped, and the resulting current from faradaic processes occurring at the electrode (caused by the potential step) is monitored as a function of time. Using this approach, we can apply the oxidation potential (OP) and reduction potential (RP) determined from the previous CV experiments to each azurin variant layer. The application of the OP and measurement of the current was defined as the 'Write' step (The electron flows into azurin molecule). In contrast, the application of the RP produces an outflow of electrons from the azurin molecules. Using this concept, a 2-state biomemory function was established. In the case of the Co-type azurin, a 210.03 mV of OP and 74.10 mV of RP were applied and the inflow and outflow of electrons was measured. The electrons were flowing into the immobilized azurin molecule when the OP was applied to the fabricated electrode, which was assigned an information value of '1'. In contrast, when the RP was applied, which was assigned an information value of '0', the stored electrons were released from the azurin. FIG. 6a show a schematic of this current response. With these currents values, the stored charge with Co-type azurin layer was calculated from Eq. (1).

$$Q=\int i dt \qquad (1)$$

The amount charge stored to Co-type azurin by writing or erasing was calculated from the currents of CA. And it was calculated to be approximately z 107×10-8 C. Also, the surface coverage of Co-type azurin was obtained from Eq. (2).

$$I_p=(n^2F^2/4RT)TAv \qquad (2)$$

(Ip: CA current, n: scan rate, G: surface coverage, n: number of electrons transferred, A: surface area of Co-type azurin immobilization, F: Faraday constant, R: gas constant, T: temperature).[25,26] According to Eq. (2), the CA current is proportional to the surface coverage. But, it needed to some assumptions that the shape of azurin molecule is spherical and the azurin molecule was self-assembled onto defined Au surface with monolayer, also, the electrode surface has homogeneous conditions without any cavities for calculating the surface coverage theoretically. So, the amount of surface coverage in co-type azurin is estimated to be≈2.278 nmol/cm$^2$ when OP aligned. Also, The Ni-type azurin (OP: 172.90 mV, RP: 51.60 mV), Fe-type azurin (OP: 236.09 mV, RP: 105.12 mV), Mn-type azurin (OP: 132.61 mV, RP: 24.97 mV) displayed a similar phenomenon. Thus, based on this electron transfer behavior, we should be able to reliably control the current flow. In conclusion, we successfully developed a 2-state memory chip that store 4 information values.

2.5. Assessment of the WRER-Type, WORM-Type Memory Test by OCPA

Previously, we proposed a 2-state memory function which had just a 'write' function and 'erase' function. However, that technique was limited in regards to reading the stored charge. To address this problem, an additional parameter needs to be assigned, which was obtained from the OCP experiments. Each azurin variant reached a stable equilibrium state between assembled azurin and electrolytes when the OCP was applied. If we apply the OCP to the reduced azurin, it will be oxidized and the electrons will be discharged according to the same principle with which the azurin reached a state of equilibrium between the two directional currents, one flowing into the electrode and the other flowing out of the electrode when no potential was applied to the system. Therefore, the OCP state can be utilized as a reading step in the memory device. The application of the OP and measurement of the current was defined as the 'Write' step (Electron inflow). The application of the open circuit potential and measurement of the conducted current was defined as the 'Read' step (Electron outflow). Using this approach, the OP and OCP were applied to the assembled azurin layer one after the other, and switching between the 'Write' and 'Read' functions could be repeated. In other words, three parameters were used to program the device with write, read and erase functions using the OP, OCP and RP, respectively. The RP performed the artificial 'Erase' step by releasing all of the trapped charges. Therefore, using this device we were able to store/read/release information by regulating the recombinant azurin variants with these three conducting states. We have concluded the directly immobilized azurin variants layers have three distinct conducting states. Briefly, in the case of the Co-type azurin, applying of an OP (210.03 mV) resulted in the transfer of electrons from the immobilized azurin layer into the Au substrate, and positive charges were stored in the azurin layer. The opposite process occurred during the reduction step. When the RP (74.10 mV) was applied, the electrons were transferred back into the azurin layer and the stored charge was erased. The OCP (182.11 mV) was then used to read these charged states. These three states were based on the OCPA (open circuit potential amperometry) experiments. FIG. 6b shows the WRER-type memory behavior according to the applied potential for the Ni-type Azurin. In this case, the memory parameter of the Ni-type azurin was as follows; OP: 172.90 mV, OCP: 121.42 mV, RP: 51.60 mV. The WRER-type memory was performed for the other metal-substituted azurin devices. In the case of Fe-type azurin (OP: 236.09 mV, OCP: 154.76 mV, RP: 105.12 mV), the other functions were performed for WORM type memory. An OP of 236.09 mV could reproducibly charge the device. A continuous set of two OCP pulses of 154.76 mV with small disconnecting times produced the necessary current responses and these charges maintained the oxidized state of the memory device. Finally, a RP pulse of 51.60 mV erased all of the stored charge. FIG. 6c shows the basic mechanism of WORM-type memory performance. The Mn-type azurin (OP: 132.61 mV, OCP: 104.26 mV, RP: 24.97 mV) also displayed a WORM-type current response with three defined parameters. In this case, when an OCP of 121.42 mV was applied at very small disconnecting time to read the stored information 3 times, the observed current responses of the stored charge could be read 3 times. These results are shown in FIGS. 6c and 6d respectively.

Overall, each azurin variant of the W-R-E-R full cycles and W-OR-M full cycles could be reliably operated at the given potentials. To perform multi-functional biomemory behavior, the different given potentials were applied to each azurin variants-immobilized biomemory chip. These results validated the biomemory concept proposed in this study. It is usually difficult for biomolecules, particularly proteins, to be successfully used into electronic devices because of their intrinsic problems, including their instability in storing different information. However, this study demonstrated that biomolecules with various functions can be applied to electronic devices to produce biomemory devices with functions and ultra-high density equivalents to the brain or retina. Multifunctions could be performed using this biomemory device, which is not possible in current silicon-based memory devices. Furthermore, the biomemory device constructed here can be directly applied to a practical memory device in the near future if a low electrochemical signal from a few single proteins can be achieved.

3. Conclusion

In this study, a multi-functional biomemory device was developed to store different types of information. For this purpose, a cysteine-modified azurin was altered to contain various metal ions. The UV-VIS study showed that the recombinant azurin molecule could bind to the various metal ions. The AFM results showed that each azurin variant layer was well formed and organized. The CV and OCP results demonstrated that these azurin variants molecules had different redox potentials and OCP compared to the original azurin molecule. Various memory functions were demonstrated using chronoamperometry (CA) and open circuit potential amperometry (OCPA) at different parameters. The recombinant azurin variants can be used to store electrons, which aligns the specific current state. As a result, the basic concept of a multi-functional biomemory chip was well established. The results presented here provide a new dimension, concept and material combination for the development of a biomemory system. In the near future, this biomemory device holds promise as a powerful alternative to silicon-based chips and can be used to perform multiple memory functions.

REFERENCES

1. Petty M C. Molecular electronics from principles to practice. Chichester: Wiley; 2007. 42-48.
2. Lieber C M, Lu W. Nanoelectronics from the bottom up. *Nat Mater* 2007; 6: 841-50.
3. Win M N, Smolke C D. Higher-order cellular information processing with synthetic RNA devices. *Science* 2003; 322; 456-60.
4. Willner I, Katz E. Bioelectronics: from theory to applications. Weinheim: Wiley-VCH; 2005. 471-476.
5. Baron R, Lioubashevski O, Katz E, Niazov T, Willner I, Elementary arithmetic operations by enzymes: a model for metabolic pathway based computing. *Angew Chem Int Ed* 2006; 45: 1572-6.
6. Liu Z, Yasseri A A, Lindsay J S, Boician D F. Molecular memories that survive silicon device processing and real-world operation. *Science* 2003; 302: 1543-5.
7. Tsen R J, Chan R, Tung V C, Yang Y. Anisotropy in organic single-crystal photovoltaic characteristics. *Adv Mater* 2008; 20: 435-8.
8. Tseng R J, Tsai C, Ma L, Ouyang J, Ozkan J, Yang Y. Digital memory device based on tobacco mosaic virus conjugated with nanoparticles. *Nat Nanotechnol* 2006; 1: 72-7.
9. Amsinck C J, Spigna N H D, Nackashi D P, Franzon P D, Scaling constraints in nanoelectronic random-access memories. *Nanotechnology.* 2005; 16: 2251-60.
10. Tomizaki K, Mihara H. Phosphate-mediated molecular memory driven by two different protein kinases as information input elements. *J Am Chem Soc* 2007; 129: 8345-52.
11. Choi J W, Fujihara M. Molecular-scale biophotodiode consisting of a green fluorescent protein/cytochrome c self-assembled heterolayer. *Appl Phys Lett* 2004; 84: 2187-9.
12. Nam Y S, Choi J W, Lee W H. Photoelectrical properties of molecular layer consisting of chlorophyll a/ferredoxin heterostructure. *Appl Phys Lett* 2004; 84: 6275-7.
13. Lee W, Oh B K, Bae Y M, Paek S H, Lee W H, Choi J W. Fabrication of self-assembled protein A monolayer and its application as an immunosensor. *Biosens Bioelectron* 2003; 19: 185-92.
14. Oh B K, Kim Y K, Park K W, Lee W H, Choi J W. Surface plasmon resonance immunosensor for the detection of *Salmonella typhimurium*. *Biosens Bioelectron* 2004; 19: 1497-504.
15. Choi J W, Park K W, Lee D B, Lee W, Lee W H. Cell immobilization using self-assembled synthetic oligopeptide and its application to biological toxicity detection using surface plasmon resonance. *Biosens Bioelectron* 2005; 20: 2300-5.
16. Choi J W, Nam Y S, Lee W. Bioelectronic device consisting of self-assembled biomolecules. *Curr Appl Phys* 2002; 2: 79-84.
17. Choi J W, Oh B K, Kim Y J, Min J. Protein-based biomemory device consisting of the cysteine-modified azurin. *Appl Phys Lett* 2007; 91. 263902(1)-(3).
18. Lee T, Kim S U, Min J, Choi J W. Multi-level biomemory device consisting of recombinant azurin/cytochrome c. *Adv Master* 2010; 22: 510-4.
19. Lee T, Kim S U, Lee J H, Min J, Choi J W. Fabrication of nano scaled protein monolayer consisting of cytochrome c on self-assembled 11-MUA layer for bioelectronic device. *J Nanosci Nanotechnol* 2009; 9: 7136-40.
20. Kim S U, Lee J H, Lee T, Min J, Choi J W. Nanoscale film formation of recombinant azurin variants with various cysteine residues on gold substrate for bioelectronic device. *J Nanosci Nanotechnol* 2010; 10: 3241-5.
21. Kim S U, Yagati A K, Min J, Choi J W. Biomemory device composed of mutant azurin thin films modified by site-directed mutagenesis. *Thin Solid Films* 2009; 518: 682-7.
22. Bonander N, Vanngard T, Tsai L C, Langer V, Nar H, Sjolin L. The metal site of *Pseudomonas aeruginosa* azurin, reveled by a crystal structure determination of the Co(II) derivative and Co-EPR spectroscopy. Proteins: *Struct Funct Bioinf* 1997; 27: 385-94.
23. Czernuszewicz R S, Fraczkiewicz G, Zareba A A. A detailed resonance Raman spectrum of nickel(II)-substituted *Pseudomanas aeruginosa* azurin. *Inorg Chem* 2005; 44: 5745-52.
24. Bhyrappa P, Sankar M, Varghese B. Mixed substituted porphyrins: structural and electrochemical redox properties. *Inorg Chem* 2006; 45: 4136-49.
25. Prodromidis M I, Florou A B, Tzouwara-Karayanni S M, Karayannis M I. The importance of surface coverage in the electrochemical study of chemically modified electrodes. *Electroanalysis* 2000; 12: 1498-501.
26. Yagati A K, Jung M, Kim S U, Min J, Choi J W. Nanoscaled redox active protein adsorption on Au-dot arrays: an electrochemical scanning probe microscopic investigation for application in nano-biodevices. *Thin Solid Films* 2009; 518: 634-7.

The invention claimed is:

1. A method for fabricating a biomemory device which is a write once read many (WORM) type device or a write read erase read (WRER) type device, comprising:
   (a) substituting an original metal ion of a metalloprotein having a redox potential with metal ion which is different from the original metal ion, and is magnesium, vanadium, manganese, iron, nickel, zinc, molybdenum, cobalt, gallium, bismuth, gold, aluminum, platinum, chromium, silver, antimony, thallium, cadmium, mercury, lead, calcium, or selenium,
   wherein the metalloprotein is azurin, hemoglobin, myoglobin, hemerythrin, cytochrome, iron-sulfur protein, rubredoxin, plastocyanin, ferritin, ceruloplasmin, carbonic anhydrase, vitamin $B_{12}$-dependent enzyme, nitrogenase, superoxide dismutase, chlorophyll-containing protein, calmodulin, glucose 6-phosphatase, hexokinase, DNA polymerase, vanabin, arginase, catalase, hydrogenase, iron-responsive element-binding protein, aconitase, urease, cytochrome oxidase, laccase, alcohol dehydrogenase, carboxypeptidase, aminopeptidase, β-amyloid, nitrate reductase, glutathione peroxidase, metallothionein, or phosphatase, and is a recombinant protein into which a cysteine residue is introduced; and
   (b) immobilizing the metalloprotein on a substrate.

* * * * *